US008709497B2

(12) United States Patent
Blotsky et al.

(10) Patent No.: US 8,709,497 B2
(45) Date of Patent: Apr. 29, 2014

(54) MINERAL, NUTRITIONAL, COSMETIC, PHARMACEUTICAL, AND AGRICULTURAL COMPOSITIONS AND METHODS FOR PRODUCING THE SAME

(76) Inventors: Roger D. Blotsky, Goodyear, AZ (US); Ramon Figueroa, Miami, FL (US)

( * ) Notice: Subject to any disclaimer, the term of this patent is extended or adjusted under 35 U.S.C. 154(b) by 1792 days.

(21) Appl. No.: 10/725,729

(22) Filed: Dec. 2, 2003

(65) Prior Publication Data

US 2005/0118279 A1 Jun. 2, 2005

(51) Int. Cl.
*A01N 59/16* (2006.01)
*A61K 33/24* (2006.01)

(52) U.S. Cl.
USPC .............. 424/617; 23/299; 23/304; 209/172; 502/60

(58) Field of Classification Search
None
See application file for complete search history.

(56) References Cited

U.S. PATENT DOCUMENTS

| | | | |
|---|---|---|---|
| 3,092,111 A | 6/1963 | Saperstein et al. | |
| 3,617,215 A * | 11/1971 | Sugahara et al. | 423/335 |
| 3,990,885 A | 11/1976 | Baillie et al. | |
| 4,150,093 A | 4/1979 | Kaminsky et al. | |
| 4,163,800 A | 8/1979 | Wickett | 514/634 |
| 4,299,826 A | 11/1981 | Luedders | 514/29 |
| 4,533,459 A * | 8/1985 | Dente et al. | 208/391 |
| 4,904,627 A * | 2/1990 | Bhattacharyya | 502/63 |
| 5,935,584 A | 8/1999 | Guerrero et al. | |
| 5,939,085 A | 8/1999 | Jacobs et al. | |
| 6,042,839 A | 3/2000 | Lahanas et al. | |
| 6,294,179 B1 | 9/2001 | Lee et al. | |
| 6,432,430 B1 | 8/2002 | Fitzjarrell | |
| 6,764,991 B2 | 7/2004 | Puvvada et al. | |
| 7,074,565 B2 * | 7/2006 | Dunbar et al. | 435/6.1 |
| 7,575,772 B2 | 8/2009 | Shi et al. | |
| 2002/0069685 A1 * | 6/2002 | Adam | 71/11 |
| 2003/0049225 A1 | 3/2003 | Rucker | |
| 2003/0108624 A1 | 6/2003 | Kosbab | 424/729 |
| 2003/0224028 A1 | 12/2003 | Galey | |
| 2004/0081712 A1 | 4/2004 | Hermansen | 424/757 |
| 2004/0161435 A1 | 8/2004 | Gupta | |
| 2004/0258597 A1 * | 12/2004 | Michalakos et al. | 423/245.3 |
| 2006/0093685 A1 | 5/2006 | Mower et al. | |
| 2007/0031462 A1 | 2/2007 | Blotsky et al. | |
| 2007/0082106 A1 | 4/2007 | Lee et al. | |
| 2007/0116832 A1 | 5/2007 | Prakash | 426/548 |
| 2007/0148186 A1 | 6/2007 | Ketzis | |
| 2007/0190173 A1 | 8/2007 | Blotsky et al. | |
| 2009/0226545 A1 | 9/2009 | Blotsky | 424/725 |

FOREIGN PATENT DOCUMENTS

| | | |
|---|---|---|
| JP | 2001294896 | 10/2001 |
| WO | WO/2007/149410 | 12/2007 |
| WO | WO 2009/023975 | 2/2009 |
| WO | WO/2009/049246 | 4/2009 |

OTHER PUBLICATIONS

International Search Report for PCT Application No. PCT/US2007/014229 dated Jun. 13, 2008.
Restriction Requirement mailed Mar. 8, 2007 (U.S. Appl. No. 11/472,536).
Response to Restriction Requirement filed May 14, 2007 (U.S. Appl. No. 11/472,536).
Non-Final Rejection mailed Jun. 15, 2007 (U.S. Appl. No. 11/472,536).
Response after Non-Final Action filed Sep. 17, 2007 (U.S. Appl. No. 11/472,536).
Final Rejection mailed Nov. 26, 2007 (U.S. Appl. No. 11/472,536).
Amendment after Final Rejection filed Jan. 28, 2008 (U.S. Appl. No. 11/472,536).
Advisory Action mailed Feb. 13, 2008 (U.S. Appl. No. 11/472,536).
Response after Final Action with Request for Continued Examination filed Mar. 27, 2008 (U.S. Appl. No. 11/472,536).
Restriction Requirement mailed Jun. 20, 2008 (U.S. Appl. No. 11/472,536).
Response to Restriction Requirement filed Nov. 20, 2008 (U.S. Appl. No. 11/472,536).
Non-Final Rejection mailed Feb. 5, 2009 (U.S. Appl. No. 11/472,536).
Response after Non-Final Action filed Jul. 6, 2009 (U.S. Appl. No. 11/472,536).
Final Rejection mailed Oct. 9, 2009 (U.S. Appl. No. 11/472,536).
Response after Final Action with Request for Continued Examination filed Feb. 9, 2010 (U.S. Appl. No. 11/472,536).
Non-Final Rejection mailed Feb. 19, 2010 (U.S. Appl. No. 11/472,536).
Examiner Interview Summary mailed May 25, 2010 (U.S. Appl. No. 11/472,536).
Response to Interview Summary filed Jun. 25, 2010 (U.S. Appl. No. 11/472,536).
Response after Non-Final Action filed Jul. 19, 2010 (U.S. Appl. No. 11/472,536).
Non-Final Rejection mailed Oct. 4, 2007 (U.S. Appl. No. 11/638,311).
Response after Non-Final Action filed Feb. 4, 2008 (U.S. Appl. No. 11/638,311).

(Continued)

*Primary Examiner* — Hasan Ahmed
(74) *Attorney, Agent, or Firm* — Ballard Spahr LLP

(57) ABSTRACT

Mineral, cosmetic, pharmaceutical, agricultural, nutraceutical, and other compositions are produced using a mineral composition containing minimal concentrations of cadmium, lead, arsenic, and mercury and containing relatively high concentrations of micro and macro mineral elements, of rare earth elements, of calcium, and of silica. The mineral concentrations are produced by processing naturally occurring clay soil to concentrate mineral elements naturally occurring in the soil.

21 Claims, 1 Drawing Sheet

(56) References Cited

OTHER PUBLICATIONS

Restriction Requirement mailed Apr. 29, 2008 (U.S. Appl. No. 11/638,311).
Response to Restriction Requirement filed May 29, 2008 (U.S. Appl. No. 11/638,311).
Notice of Information or Non-Responsive Amendment mailed Jul. 28, 2008 (U.S. Appl. No. 11/638,311).
Response to Restriction Requirement filed Aug. 1, 2008 (U.S. Appl. No. 11/638,311).
Final Rejection mailed Oct. 20, 2008 (U.S. Appl. No. 11/638,311).
Response after Final Action with Request for Continued Examination filed Apr. 20, 2009 (U.S. Appl. No. 11/638,311).
Non-Final Rejection mailed Jun. 19, 2009 (U.S. Appl. No. 11/638,311).
Response after Non-Final Action filed Dec. 21, 2009 (U.S. Appl. No. 11/638,311).
Final Rejection mailed Mar. 31, 2010 (U.S. Appl. No. 11/638,311).
Examiner Interview Summary mailed May 28, 2010 (U.S. Appl. No. 11/638,311).
Response to Interview Summary filed Jun. 25, 2010 (U.S. Appl. No. 11/638,311).
Response after Final Action with Request for Continued Examination filed Jul. 30, 2010 (U.S. Appl. No. 11/638,311).
International Search Report mailed Jun. 13, 2008 (WO/2007/149410).
International Preliminary Report on Patentability and Written Opinion mailed Jun. 13, 2008 (WO/2007/149410).
Ames BN, Shigenaga MK, Hagen TM. (1993) Oxidants, antioxidants, and the degenerative diseases of aging. Proc Natl Acad Sci USA. 90(17): 7915-7922.
Blando F, Gerardi C, Nicoletti I. (2004) Sour Cherry (*Prunus cerasus* L) Anthocyanins as Ingredients for Functional Foods. J Biomed Biotechnol. 2004(5): 253-258.
Ou B, Hampsch-Woodill M, Prior RL. (2001) Development and validation of an improved oxygen radical absorbance capacity assay using fluorescein as the fluorescent probe. J Agric Food Chem. 49(10): 4619-4626.
International Preliminary Report on Patentability and Written Opinion mailed Apr. 13, 2010 (WO/2009/049246).
International Search Report mailed Jan. 8, 2009 (WO/2009/049246).
Restriction Requirement mailed Dec. 15, 2009 (U.S. Appl. No. 12/249,798).
Response to Restriction Requirement filed Feb. 11, 2010 (U.S. Appl. No. 12/249,798).
Non-Final Rejection mailed Apr. 9, 2010 (U.S. Appl. No. 12/249,798).
Response after Non-Final Action filed Jul. 9, 2010 (U.S. Appl. No. 12/249,798).
Final Rejection mailed Jul. 14, 2010 (U.S. Appl. No. 12/249,798).
Rahbar S, Figarola JL. (2002) Inhibitors and Breakers of Advanced Glycation Endproducts (AGEs): A Review. Curr. Med. Chem.—Imun., Endoc. & Metab. Agents, 2: 135-161.
Li F, Wang CN, Zhou Y, Xiong WW. (2006) Analysis of contents of copper and cadmium in *Siraitia grosvenori*. Welling Yuansu Yu Jiankang Yanjiu, 23(6): 30-34.
Anjos S, Polychronakos C. (2004) Mechanisms of genetic susceptibility to type I diabetes: beyond HLA. Mol. Gen. Metabolism, 81: 187-195.
Jafar-Mohammadi B, McCarthy MI. (2008) Genetics of type 2 diabetes mellitus and obesity—a review. Annals Medicine, 40: 2-10.
Dignan P. (1981) Teratogenic Risk and Counseling in Diabetes. Clin Obstet Gynecol., 24(1): 149-159.
Field LL. (2002) Genetic linkage and association studies of Type I diabetes: challenges and rewards. Diabetologia, 45 (1):21-35.

Greiner DL, Rossini AA, Mordes JP. (2001) Translating data from animal models into methods for preventing human autoimmune diabetes mellitus: caveat emptor and primum non nocere. Clin Immunol., 100(2): 134-143.
Simpson RW, Shaw JE, Zimmet PZ. (2003) The prevention of type 2 diabetes—lifestyle change or pharmacotherapy? A challenge for the 21st century. Diabetes Res Clin Pract., 59(3): 165-180.
Rich SS, Onengut-Gumuscu S, Concannon P. (2009) Recent progress in the genetics of diabetes. Horm Res., 71 (Supp 1): 17-23.
Wicker LS, Moule CL, Fraser H, Penha-Goncalves C, Rainbow D, Garner VE, Chamberlain G, Hunter K, Howlett S, Clark J, Gonzalez-Munoz A, Cumiskey AM, Tiffen P, Howson J, Healy B, Smink LJ, Kingsnorth A, Lyons PA, Gregory S, Rogers J, Todd JA, Peterson LB. (2005) Natural genetic variants influencing type 1 diabetes in humans and in the NOD mouse. Novartis Found Symp., 267: 57-65.
Ikegami H, Fujisawa T, Ogihara T. (2004) Mouse models of type 1 and type 2 diabetes derived from the same closed colony: genetic susceptibility shared between two types of diabetes. ILAR J., 45(3): 268-277.
Suzuki YA, Murata Y, Inui H, Sugiura M, Nakano Y. (2005) Triterpene glycosides of *Siraitia grosvenori* inhibit rat intestinal maltase and suppress the rise in blood glucose level after a single oral administration of maltose in rats. J Agric Food Chem., 53(8): 2941-2946.
Response to Non-Final Rejection filed Mar. 28, 2011 for U.S. Appl. No. 11/472,536, filed Jun. 21, 2006 (1$^{st}$ Named Inventor—Blotsky) (16 pages).
Final Rejection mailed Jun. 8, 2011 for U.S. Appl. No. 11/472,536, filed Jun. 21, 2006 (1$^{st}$ Named Inventor—Blotsky) (15 pages).
Response to Final Rejection filed Nov. 8, 2011 for U.S. Appl. No. 11/472,536, filed Jun. 21, 2006 (1$^{st}$ Named Inventor—Blotsky) (12 pages).
Response to Non-Final Rejection filed Mar. 28, 2011 for U.S. Appl. No. 11/638,311, filed Dec. 12, 2006 (1$^{st}$ Named Inventor—Blotsky) (15 pages).
Final Rejection mailed Jun. 8, 2011 for U.S. Appl. No. 11/638,311, filed Dec. 12, 2006 (1$^{st}$ Named Inventor—Blotsky) (16 pages).
Response to Final Rejection filed Nov. 8, 2011 for U.S. Appl. No. 11/638,311, filed Dec. 12, 2006 (1$^{st}$ Named Inventor—Blotsky) (13 pages).
Amendment filed Jun. 29, 2011 with the European Patent Office for EP Application No. 08838086.0 filed on Oct. 10, 2008 (Applicant—Global Organics // 1$^{st}$ Named Inventor—Blotsky) (8 pages).
Requirement for Restriction/Election mailed Jun. 2, 2011 for U.S. Appl. No. 12/497,387, filed Jul. 2, 2009 (1$^{st}$ Named Inventor—Blotsky) (9 pages).
Response to Requirement for Restriction/Election filed Dec. 2, 2011 for U.S. Appl. No. 12/497,387, filed Jul. 2, 2009 (1$^{st}$ Named Inventor—Blotsky) (11 pages).
Non-Final Rejection mailed Dec. 27/ for U.S. Appl. No. 12/497,387, filed Jul. 2, 2009 (1$^{st}$ Named Inventor—Blotsky) (7 pages).
Product Description for Low-Carb Natural Sweetner made by TriMedica (retrieved from www.gnpd.com), May 2004.
Xiangyang Q, Weijun C, Liegang L. Pint Y, Bijun X, (2006) Effect of a *Siraitia grosvenori* extract containing mogrosides on cellular immune system of type 1 diabetes mellitus mice. Mol Nutr Food Res. 50(8): 732-738.
Extended European Search Report issued Dec. 9, 2010 for EP Application Serial No. 08838086.0 (now EP Publication No. 2207420), which claims priority to PCT/US08/079632 filed on Oct. 10, 2008 (Inventor: Blotsky et al.; Applicant: Global Organics LLC).
Non-Final Office Action issued Oct. 27, 2010 for U.S. Appl. No. 11/472,536, filed Jun. 21, 2006 (Inventor: Blotsky et al.).
Non-Final Office Action issued Oct. 27, 2010 for U.S. Appl. No. 11/638,311, filed Dec. 12, 2006 (Inventors: Blotsky et al.).
Response to Final Office Action filed Oct. 14, 2010 for U.S. Appl. No. 12/249,798, filed Oct. 10, 2008 (Inventor: Blotsky et al.).
Non-Final Rejection mailed Dec. 17, 2013 for U.S. Appl. No. 11/472,536, filed Jun. 21, 2006 (Inventors—Blotsky et al.) (12 pages).
Summary of Examiner Interview mailed Dec. 5, 2013 for U.S. Appl. No. 11/472,536, filed Jun. 21, 2006 (Inventor—Blotsky et al.) (2 pages).

(56) References Cited

OTHER PUBLICATIONS

Non-Final Rejection mailed Dec. 16, 2013 for U.S. Appl. No. 11/638,311, filed Dec. 12, 2006 (Inventors—Blotsky et al.) (13 pages).

Summary of Examiner Interview mailed Dec. 5, 2013 for U.S. Appl. No. 11/638,311, filed Dec. 12, 2006 (Inventors—Blotsky et al.) (2 pages).

* cited by examiner

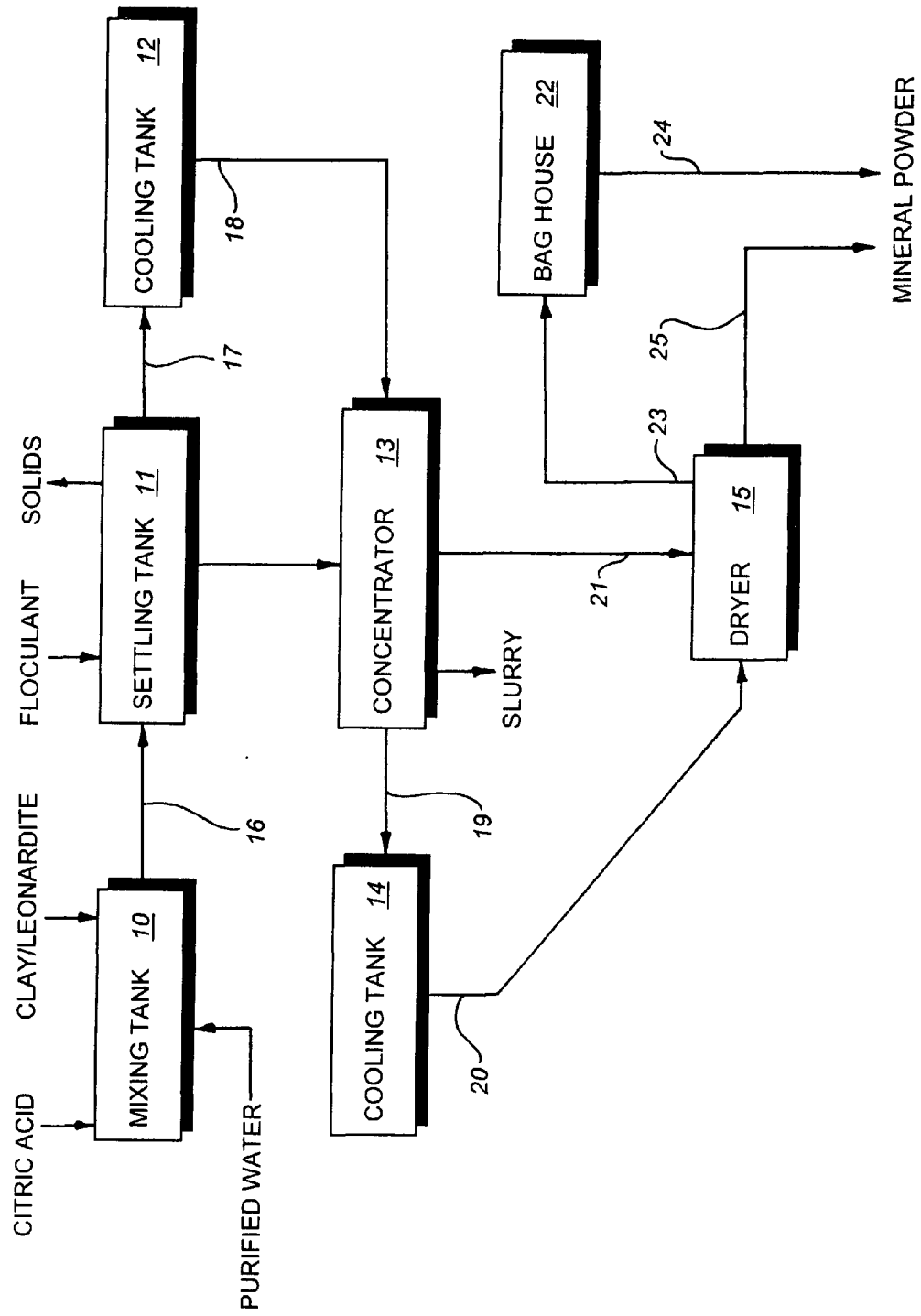

MINERAL, NUTRITIONAL, COSMETIC, PHARMACEUTICAL, AND AGRICULTURAL COMPOSITIONS AND METHODS FOR PRODUCING THE SAME

This invention pertains to mineral, cosmetic, pharmaceutical, agricultural, nutraceuticals, and other compositions and methods for producing the same.

More particularly, this invention pertains to a method for producing compositions including an unusually large number of naturally occurring minerals.

In a further respect, the invention pertains to a mineral composition that has an unusually low pH but that does not irritate dermal tissues when applied thereto.

In another respect, the invention pertains to nutritional, cosmetic, and pharmaceutical compositions that include a significant number of mineral elements and that facilitate delivery of the minerals into the body of a human being or animal.

The following definitions are utilized herein.

Chemical element. Any of more than 100 fundamental metallic and nonmetallic substances that consist of atoms of only one kind and that either singly or in combination constitute all matter, most of these substances lighter in weight than and including uranium being found in nature and the rest being produced artificially by causing changes in the atom nucleus.

Clay. A natural or synthetic colloidal lusterless earthy composition that includes tiny sheet-like layered particles of alumina and/or silica that are less than about 0.002 millimeters in size, that is generally plastic when moist, and that, when naturally occurring, includes decomposed igneous and/or metamorphic rocks. Most clays have a pH in the range of about 4.5 to 8.5. Natural and synthetic clays include mineral elements. Clays can, in additional to having particles less than five microns in size, include particles having a size greater than five microns.

Leonardite. A soft, loose-textured coal that has low BTU value. Leonardite is a humate; can include up to 70% by weight minerals; can be formed from lignite; can occur naturally as the result of not being heated and pressurized over time to the extent necessary to produce anthracite, lignite, or bituminous coal; and, can include compost as a component.

Mineral. Any naturally occurring chemical element or compound. A mineral has a characteristic crystal structure and chemical composition or range of compositions.

Mineral element. A chemical element that occurs naturally as or in a mineral. A mineral element may be produced using synthetic or manufacturing processes; however, each mineral element does occur naturally as or in a mineral.

Rare earth or rare earth element. Any one of a group of metallic elements with atomic numbers 58 through 71, including cerium, praseodymium, neodymium, promethium, samarium, euro0pium, gadolinium, terbium, dysprosium, holmium, erbium, thulium, ytterbium, and lutetium. In nature, rare earth elements are bound in combination with nonmetallic elements in the form of phosphates, carbonates, fluorides, silicates, and tantalates.

Sand. A loose material consisting of small but easily distinguishable grains usually less than two millimeters in diameter and more than about 0.02 millimeters in diameter, most commonly of quartz, resulting from the disintegration of rocks.

Silt. Unconsolidated or loose sedimentary material whose constituent rock particles are finer than grains of sand and larger than clay particles, specifically, material consisting of mineral soil particles ranging in diameter from about 0.02 to 0.002 millimeters.

Mineral elements are essential to life. The body however does not manufacture a single mineral element although all tissue and internal fluids contain them from bones, teeth, soft tissue, muscle, blood and nerve cells. The usefulness of mineral elements and of trace mineral elements in biological systems has been scientifically and medically established. Their complimentary function for enhancing nutrient exchange, improved conductivity of cellular transport, support essential osmotic balance of every tissue, fluid, cell and organ, and play a role on everything from muscle response, to transmission of messages through the nervous system, the production of hormones, digestion, and utilization of nutrients. They play a significant role in disease prevention not only in the functions described above, but on a genetic fundamental level, as biological systems require mineral elements to effectively and accurately program DNA synthesis required for cell replication. Any defective programming in DNA synthesis by deficient mineral element function could lead to abnormal replication and alternatively promote disease state or death.

The presence in the body of many mineral elements is the result of supplementation through diet. Macro mineral elements are those that the body requires in greater quantities than 100 mg daily, while Micro mineral elements are those that the body requires less than 100 mg daily. Food consumption, particularly of fruits and vegetables, is the only means to supplement vital mineral elements to the body. The introduction of processed food and the insurgence of soil mineral depletion have created a food market less apt to derive and deliver the mineral element requirements that were once delivered only by consumption. Today's synthetic vitamin and mineral element supplement market (which is valued in the billions of dollars) has been established on the basis that the human body is not getting all the necessary mineral elements through normal food consumption.

Soil depletion phenomena are real and measurable. Restoration of soil involves methods of crop re-cycling and use or organic fertilizers to help reconstitute the mineral content of soil. The use of organic fertilizers has been increasing in usage over the last three decades. Their increased usage is the result of environmental and agricultural concerns for moving towards a chemical-free and pesticide-free method of crop production coupled with a means for replenishment that can alleviate the soil depletion of minerals on farms overburdened by decades of use.

Soil taxonomy and the many sub-classifications yield earth matter that collectively includes all known natural minerals. Soils vary in their mineral content with some having predominant concentration a certain minerals and trace minerals. The minerals can be concentrated from the soil using extraction techniques known in the art and are usually identified and quantified by analytical equipment.

In all cases, soil classification and the extraction techniques applied to capture or recover minerals are the limiting factors in maximizing the total number and amounts of minerals identified and quantified. Most extraction techniques fail to capture a wide spectrum of inherent minerals found in soil.

One facet of the invention pertains to extraction techniques used to gather, isolate, and concentrate specific mineral elements. For example, U.S. Pat. Nos. 4,150,093 Kaminsky and 3,990,885 Baillie describe hot water extraction of tar sands yielding heavy minerals at specific high concentrations of titanium and zirconium.

Clay soil is one of the three principal types of general soil classifications, the other two being sandy soil and loamy soil. Most soils include silt.

The extraction techniques described herein relates in part to specific soils and soil combination compositions having taxonomic classifications including clay soil, sandy soil, and/or clay-sand soil comprising a combination of clay soil and sandy soil. Sandy soil typically is described as silicates. Soils classified as clay soils contain a significant percentage of clay in their composition, typically at least twenty percent by weight.

Soil includes very coarse, coarse, fine, very fine, and medium size particle sizes. The coarse particles ranges in size from 0.5-1.0 mm. The fine particles are from about 0.10 mm to 0.25 mm in size. The medium particles are from 0.25-0.50 mm in size. Very coarse particles are greater than about 1.0 mm in size. The very fine particles are less than about 0.10 mm in size.

The percent sand in clay-sand soil typically by definition equals or is greater than 20% by weight. The percent of silt in clay-sand soil typically by definition equals or is greater than 20% by weight.

Two samples of selected soil were analyzed by A&L laboratories in Memphis, Tenn. with the following results:

| Soil Sample | Classification | % Clay | % Sand | % Silt |
|---|---|---|---|---|
| Site # 4 | Clay | 22.5 | 36.5 | 40.9 |
| Site # 5 | Clay | 23.1 | 24.4 | 52.5 |

The soils from Sites 4 and/or 5 or other sites were collected and subjected to the aqueous extraction process described below to produce both a liquid mineral element composition containing mineral elements and to produce a dry powder mineral element composition. The dry powder mineral element composition is produced by drying the liquid mineral element composition.

Both the liquid mineral element composition and the dry powder mineral element composition capture and recover similar mineral elements to constitute a comprehensive mineral composition. Both liquid and dry powder mineral element compositions produced by the procedures described herein preferably, but not necessarily, contain a minimum of 8 macro mineral elements and a minimum of 60 micro mineral elements.

Physical testing and analysis was also conducted on the liquid and dry mineral element compositions. Typical specifications of liquid extract solution range in color but preferably are from yellow to amber brown and contain between 1 to 10% by weight of mineral elements, most preferably 3-5%. The solution is acidic with a pH ranging from 2.5-4.5, most preferably from 2.5-3.5. The liquid extract can be dried to produce an anhydrous powder. The anhydrous powder presently ranges in color from light-off-white to brown, but preferably from yellow to golden amber, is insoluble in any non-polar solvent such as hydrophobic liquids (oil and fats), is insoluble in alcohol, and is readily soluble, yet non-swelling, in water and hydro-alcoholic solutions at concentrations of 1 to 5%, most preferably at concentrations of 3-5% by weight. The dry powder is partially soluble or capable of being partially suspended in polar solvent in supersaturated solutions. The dry powder can also be easily suspended in non-polar solvents.

As stated above, both liquid and dry mineral element compositions produced by the procedures described herein will contain a minimum of 8 macro mineral elements and a minimum of 60 micro mineral elements. The micro mineral elements include trace and rare earth mineral elements.

For example, the dry mineral element composition will contain at concentrations ranging from 0.0001-20.00% by weight, most preferably from 0.001%-10% by weight, the macro mineral elements of calcium, chlorine, magnesium, manganese, phosphorous, potassium, silicon, and sodium; and, will preferably contain at least sixty micro mineral elements at concentrations ranging from 0.00001-3.0% by weight, most preferably from 0.0001-1% by weight. The micro mineral elements include aluminum, antimony, arsenic, barium, beryllium, bismuth, boron, bromine, cadmium, cerium, cesium, chromium, cobalt, copper, dysprosium, erbium, europium, fluorine, gadolinium, gold, hafnium, holmium, iodine, indium, iridium, iron, lanthanum, lead, lithium, lutetium, mercury, molybdenum, neodymium, nickel, niobium, palladium, platinum, praseodymium, rhenium, rhodium, rubidium, ruthenium, samarium, scandium, selenium, silver, strontium, sulfur, tantalum, terbium, tellurium, thallium, thorium, thulium, tin, titanium, tungsten, vanadium, ytterbium, yttrium, zinc, and zirconium.

Since the process described herein normally does not introduce any minerals as part of the extraction process, it can be established that any minerals identified and quantified by the process described herein have been captured and recovered from the initial soil matter or the starting raw material. Therefore, it can be established that the original clay or other soil that processed through the extraction method described herein likely include aluminum silicates and other metal silicates in nature which has been naturally enriched with multiple detectable minerals. It can also be established that if a mineral element is identified and quantified in the aqueous liquid extract, it will be identified and quantified in the dry powdered extract in much higher concentrations as a result of drying process or volume reduction.

For example, a lot produced using the soil and extractions methods described herein was tested by independent analytical testing for conducting chemical analysis using standard techniques of identification and quantification for both dry and liquid forms of the comprehensive mineral composition. The results of testing performed at Teledyne Wah Chang Laboratories in Huntsville, Ala., utilizing scientifically accepted and standard equipment such as Titration, Inductively Coupled Plasma, Mass Spectrometry, and Atomic Absorption equipment resulted in the mineral element quantification data set forth below in TABLE I for an aqueous mineral element composition and from the dry mineral element composition that resulted when the aqueous mineral element composition was dried to produce a powder.

TABLE I

| Element | Concentration in aqueous liquid composition | Concentration in dry powder |
|---|---|---|
| Macro Mineral Elements | | |
| Calcium | 2900 ppm | 8% |
| Chlorine | 170 mg/ml | 0.84% * |
| Magnesium | 460 ppm | 0.95% |
| Manganese | 8.6 ppm | 240 ppm |
| Phosphorous | 0.2 g/L | 0.43% |
| Potassium | 220 mg/L | 1.2% |
| Silicon | 130 mg/L | 0.36% |
| Sodium | 720 mg/L | 2.0% |
| Micro Mineral Elements | | |
| Aluminum | 540 ppm | 0.65% |
| Antimony | 460 ppb | 16.0 ppm |
| Arsenic | 11 ppm | 3.1 ppm |
| Barium | 340 ppb | 11.0 ppm |
| Beryllium | 0.29 ppm | .01 ppm |
| Bismuth | <50 ppb | <1.00 ppm |
| Boron | 2.0 mg/L | 72.00 ppm |
| Bromine | * Present as part of Chlorine assay | |
| Cadmium | <50 ppb | 1.10 ppm |
| Total Organic Carbon | 12 g/L | Trace |
| Cerium | 1600 ppb | 68.00 ppm |
| Cesium | 82 ppb | 2.00 ppm |
| Chromium | 1.8 ppm | 5.00 ppm |
| Cobalt | 0.25 ppm | 1.00 ppm |
| Copper | 0.09 ppm | <1.00 ppm |
| Dysprosium | 230 ppb | 9.00 ppm |
| Erbium | 150 ppb | 6.00 ppm |
| Europium | <50 ppb | 2.00 ppm |
| Fluorine | * Present as part of Chlorine assay | |
| Gadolinium | 220 ppb | 9.00 ppm |
| Gallium | 70 ppb | 2.40 ppm |
| Germanium | <50 ppb | <1.00 ppm |
| Gold | <50 ppm | <1.00 ppm |
| Hafnium | <0.5 mg/L | 5.00 ppm |
| Holmium | <50 ppb | 2.00 ppm |
| Iodine | * Present as part of Chlorine assay | |
| Indium | <50 ppb | Trace |
| Iridium | <50 ppb | <1.00 ppm |
| Iron | 730 ppm | 1.25% |
| Lanthanum | 650 ppb | 28.00 ppm |
| Lead | <50 ppb | <1.00 ppm |
| Lithium | 0.9 mg/L | <1.00 ppm |
| Lutetium | <50 ppb | <1.00 ppm |
| Mercury | Trace | <1.00 ppm |
| Molybdenum | 3200 ppb | 120.00 ppm |
| Neodymium | 1000 ppb | 45.00 ppm |
| Nickel | 0.74 ppm | 2.00 ppm |
| Niobium | 96 ppb | 3.00 ppm |
| Palladium | <500 ppb | <1.00 ppm |
| Platinum | <50 ppb | <1.00 ppm |
| Praseodymium | 290 ppb | 10.00 ppm |
| Rhenium | <50 ppb | <1.00 ppm |
| Rhodium | <50 ppb | <1.00 ppm |
| Rubidium | 360 ppb | 11.00 ppm |
| Ruthenium | <50 ppb | <1.00 ppm |
| Samarium | 250 ppb | 10.00 ppm |
| Scandium | <400 ppb | 4.00 ppm |
| Selenium | 0.63 mg/L | 21.00 ppm |
| Silver | <0.02 ppm | <5.00 ppm |
| Strontium | 14000 ppb | 420.00 ppm |
| Sulfur | 1.1 g/L | 1.8% |
| Tantalum | <50 ppb | <1.00 ppm |
| Terbium | <50 ppb | 2.00 ppm |
| Tellurium | <50 ppb | <1.00 ppm |
| Thallium | <50 ppb | 1.00 ppm |
| Thorium | 640 ppb | 22.00 ppm |
| Thulium | <50 ppb | 1.00 ppm |
| Tin | <50 ppb | <1.00 ppm |
| Titanium | 9.34 ppm | 210.00 ppm |
| Tungsten | 52 ppb | 17.00 ppm |
| Vanadium | 4.3 ppm | 14.00 ppm |
| Ytterbium | 140 ppb | 6.00 ppm |
| Yttrium | 1300 ppb | 61.00 ppm |

TABLE I-continued

| Element | Concentration in aqueous liquid composition | Concentration in dry powder |
|---|---|---|
| Zinc | 1.2 ppm | 14.00 ppm |
| Zirconium | 2.0 mg/L | 62.00 ppm |

The mineral element compositions set forth above in Table I were produced from naturally occurring soil the analysis of which is reflected below in Table II.

TABLE II

Analysis of Naturally Occurring Soil
Macro Mineral Elements

| Element | Concentration in ppm by weight unless noted as % (for weight percent) |
|---|---|
| Silicon | 25.0% |
| Aluminum | 9.3% |
| Potassium | 4.8% |
| Magnesium | .83% |
| Sulfur | 1.6% |
| Iron | 1.6% |
| Calcium | 4.1% |
| Titanium | 0.23% |
| Sodium | 0.138% |
| Manganese | 150 |
| Gallium | 25 |
| Molybdenum | 61 |
| Germanium | 25 |
| Iodine | 7 |
| Bromine | 5.2 |
| Tungsten | 8.1 |
| Hafnium | 2.0 |
| Tantalum | 0.50 |
| Zirconium | 10 |
| Arsenic | 0.2 |
| Antimony | 29 |
| Selenium | 4.1 |
| Zinc | 20 |
| Samarium | 3.5 |
| Holmium | 1.1 |
| Terbium | .62 |
| Iridium | .51 |
| Lutetium | .45 |
| Chromium | 70 |
| Lanthanum | 18 |
| Ruthenium | 7.8 |
| Yttrium | 1.2 |
| Indium | .38 |
| Lead (under) | 17 |
| Niobium | 2.89 |
| Carbon | .19 |
| Hydrogen | .05 |
| Nitrogen | .03 |
| Scandium | 3.7 |
| Cobalt | 4.8 |
| Ytterbium | 1.4 |
| Strontium | 240 |
| Barium | 390 |
| Gold | .68 |
| Europium | .49 |
| Neodymium | 20 |
| Cerium | 40 |
| Cesium | 183 |
| Thorium | Above 100 |
| Uranium | Above 100 |
| Nickel | 60 |
| Beryllium | .10 |
| Bismuth | 14.3 |
| Boron | 7 |
| Cadmium | 1.12 |
| Chloride | 6100 |
| Copper | 2.2 |
| Fluoride | 3.85 |
| Lithium | 1.44 |

TABLE II-continued

Analysis of Naturally Occurring Soil
Macro Mineral Elements

| Element | Concentration in ppm by weight unless noted as % (for weight percent) |
|---|---|
| Mercury | 0.166 |
| Palladium | 0.74 |
| Phosphate | 320 |
| Platinum | 0.08 |
| Rhodium | 0.44 |
| Rubidium | 36.5 |
| Silver | 0.3 |
| Tellurium | 0.1 |
| Thulium | 0.65 |
| Tin | 0.44 |
| Vanadium | 8 |
| Dysprosium | 4.0 |
| Praseodymium | 2.0 |
| Thallium | 10 |
| Rhenium | 1.0 |
| Erbium | 2.0 |
| Oxygen | 0.2 |

Once a desirable naturally occurring soil or soil combination is obtained, the soil(s) is subjected to the extraction process shown in FIG. 1 and described below in more detail. The selection of an appropriate soil or soil combination is, however, important in the practice of the invention and this process is now described. It is understood that it is possible to incorporate synthetically produced "soils" or compositions to produce soils used in the invention; however, the use of naturally occurring soils is presently preferred and it is the use of such naturally occurring soils that is now described in detail.

Clay soils, mixtures of clay soils, or mixtures of clay soil(s) and leonhardite are presently preferred in the practice of the invention. One reason such soil combinations are preferred is that such soils can be high in the mineral elements deemed important in the practice of the invention. As noted, it is preferred that mineral element compositions produced in accordance with the invention include at least eight macro mineral elements and at least sixty micro mineral elements.

The first step in determining whether a clay soil is acceptable is to determine of arsenic, lead, mercury, and cadmium are each present in acceptably small concentrations. It is presently preferred that the concentration of each of these elements be less than the concentrations shown below in Table III.

TABLE III

Maximum Desired Concentrations of Toxic Elements

| Element | Maximum Desired Soil Concentration in ppm or ppb |
|---|---|
| Arsenic | 0.2 ppm |
| Lead | 0.17 ppb |
| Mercury | 0.116 ppm |
| Cadmium | 1.12 ppm |

To achieve the desired concentrations noted above, a soil that has a greater than desired concentration of the toxic elements can be admixed with one or more soils containing a lesser than desired concentration of the toxic elements. Further, the maximum desired concentrations of the four toxic elements noted above can vary depending on the intended end use of the mineral element composition produced by the invention. For example, if the mineral element composition is intended to be used in products ingested by human beings, the acceptable levels of the toxic elements normally will be less than if the mineral element composition will be used in agricultural products.

If the soil, or soil combination, has appropriately low concentrations of the four toxic elements arsenic, lead, mercury, and cadmium, the soil is next tested to determine if acceptable concentrations of rare earth elements are present in the soil or soil combination. Desired levels of rare earth elements are set forth below in Table IV.

TABLE IV

Preferred Minimum Concentrations of Selected Rare Earth Elements in Naturally Occurring Soil

| Element | Preferred Minimum Soil Concentration in ppm |
|---|---|
| Cerium | 40 |
| Praseodymium | 2 |
| Neodymium | 20 |
| Samarium | 3.5 |
| Europium | .49 |
| Terbium | .62 |
| Dysprosium | 4 |
| Holmium | 1 |
| Erbium | 2 |
| Thulium | .65 |
| Ytterbium | 1.2 |
| Lutetium | .45 |

The concentration of the elements listed in Table IV can vary as desired, but, as noted, it is desirable to have at least the concentration of each element as noted in Table IV. A lanthanum concentration of at least eighteen ppm and a scandium concentration of at least three and seven-tenths ppm are also preferred. Concentrations of promethium and gadolinium are also desirable. In the practice of the invention, at least ten rare earth elements are present in the soil, preferably at least twelve, and more preferably all of the rare earth elements along with lanthanum and scandium. The presence of most or all of the rare earth elements in the soil, and in the mineral element compositions derived from the soil, is believed to be important in improving the efficacy of the mineral element composition when ingested by the body or when transdermally absorbed by the body.

The clay soil or soil combination also includes at least 5% by weight calcium, preferably at least 10% by weight calcium, and most preferably at least 20% by weight calcium. Concentrations of calcium of 25% by weight or greater are acceptable.

The clay soil or soil combination also includes at least 5% by weight silica, preferably at least 10% by weight silica, and most preferably at least 20% by weight silica. Concentrations of silica of 25% by weight or greater are acceptable.

The clay soil or soil combination also includes at least 0.25% by weight phosphorous, preferably at least 1% by weight phosphorous, and most preferably at least 2% by weight phosphorous.

Leonardite is a valuable mineral source in producing soils that are subjected to the extraction process illustrated in FIG. 1.

Once a clay soil or clay soil combination is obtained that contains the requisite mineral elements, the clay soil is subjected to the extraction process of FIG. 1. The following example describes the extraction process by way of illustration, and not limitation of the invention.

Example of Extraction Process

In FIG. 1, 12,000 pounds of water purified via reverse osmosis or another desired purification process, 200 pounds of citric acid, and 5000 pounds of clay soil are added to the mixing tank 10. The amount of citric acid (or of phosphoric acid or other edible acid(s)) used can be in the range of 0.25% to 7.5% of the weight of water utilized, but typically is in the range of 1.0% to 2.0%. The purified water is produced using any desired water purification technique; however, water purified by reverse osmosis is presently utilized. The water-citric acid-soil slurry is gently agitated (for example, with a blade slowly rotating at from one to ten RPM) for about an hour, although the agitation time can vary as desired. The agitation is preferably non-cavitating and is carried out without forming bubbles in the mixture.

The slurry from tank 10 is directed, as indicated by arrow 16, into a settling tank 11 to permit particulate to settle downwardly out of the slurry. The slurry is maintained in the settling tank 11 for any desired length of time, but this length of time is presently in the range of about one to ten days. As the length of time that the slurry is maintained in the settling tank 11 increases, the amount of liquid that can be drawn out of the tank and sent to cooling tank 12 or concentrator 13 increases and the amount of solids that have settled to the bottom of the tank increases. Chemicals or any other desired method can be utilized to facilitate the settling of solids from slurry directed into tank 10. After the slurry has resided in settling tank 11 for the desired period of time, liquid is drawn out of the tank to cooling tank 12, or directly to the concentrator 13. The solids on the bottom of tank 11 can be directed to tank 10 to be reprocessed, can be discarded, or can be otherwise utilized.

Cooling tank 12 cools the fluid from tank 11 to a temperature in the range of forty to seventy degrees F. (5 to 21 degrees C.). Tank 12 (and 14) is presently cooled with a refrigeration system to cool the fluid in tank 12. Consequently, when fluid contacts the inner cooled wall surfaces of tank 12, the wall surfaces transport heat away from and cool the fluid. Any desired system can be utilized to cool tank 12 (and 14) and/or to cool the fluid in the tank. For example, a coil can be placed in the fluid and cool the fluid without directly cooling the tank walls with a refrigeration or other system. The fluid from tank 11 is cooled to prevent or minimize yeast and mold growth. The fluid in tank 11 normally is heated due to the ambient temperature and not due to any chemical or mechanical action that takes places in tank 11. Cooled liquid from tank 12 is, as indicated by arrow 18, directed from tank 12 to concentrator 13.

The concentrator 13 comprises a thin film composite reverse osmosis system in which fluid is directed into a plurality of long, cylindrical, hollow liquid permeable membrane tubes under pressure; and, in which fluid is forced radially out through the liquid permeable cylindrical membrane wall to increase the concentration of the mineral elements in the fluid. Evaporation is an alternate approach to increasing the concentration of mineral elements in the fluid. A reverse osmosis system is preferable to evaporation because it requires less energy, and because the water that passes radially through the membrane is a source of clean usable water.

One preferred reverse osmosis system includes eight hollow tubes or "vessels" that are about four inches in diameter and forty inches long. Each tube houses three concentric cylindrical membranes. The permeability flow rate is approximately 80% to 95% rejection, depending on the feed rate and the concentration of mineral elements in the fluid being treated. The spacing between the three concentric membranes is about ¼ inch. There are three ring couplers and one end plug per tube. The maximum pressure allowed by the cylindrical membranes is about 600 psig. A pressure of between 300 to 450 is recommended and is normally used. The membranes are to be utilized at a temperature of 135 degrees F. (57 degrees C.) or less. The temperature of the fluid and the membrane is, however, typically maintained in the range of 55 degrees F. to 65 degrees F. (12 to 20 degrees C.). The fluid from tank 11 is processed by passing it sequentially through each of the eight tubes.

If desired, concentration systems other than reverse osmosis systems can be utilized. Such other systems are not believed comparable to a reverse osmosis system in terms of cost and efficiency.

In FIG. 1 the "slurry" by product produced by the concentrator 13 comprises clean usable water with a low concentration of mineral elements. The aqueous concentrate liquid produced by concentrator 13 is, as indicated by arrow 19, directed to cooling tank 14 or directly to dryer 15. Tank 14 cools the concentrate liquid to 40 degrees F. to 70 degrees F. (5 degrees to 20 degrees C.) to prevent the growth and yeast and mold.

The concentrate liquid produced by concentrator 13 has a pH of approximately 3. The concentrate liquid typically includes from three to twelve percent by weight mineral elements, i.e. if the mineral elements are separated from the concentrate liquid, a dry material is produced that has a weight equaling about 3% to 12% by weight of the concentrate liquid. The pH of the concentrate liquid is adjusted by varying the amount of citric acid or other edible acid and/or alkaline or acidic soil added to the mixing tank 10 and is in the range of pH 2.0 to pH 5.0, preferably pH 2.5 to pH 3.5. The pH of the concentrate liquid (and dry powder or other material produced therefrom) preferably is less than pH 4.5. Table I herein illustrates the mineral element present in one concentrate liquid produced by concentrator 13. If necessary, the concentrate liquid is recirculated back through concentrator 13 to increase the mineral element content in the liquid. As the proportion of mineral elements increases, the propensity of mineral elements to precipitate from the concentrate liquid increases. A mineral element concentration of at least eight percent is presently preferred for injection into dryer 15. A mineral element concentration in the range of three to twelve percent or more is beneficial because many prior art processes currently only produce a fluid having a mineral element concentration of about two percent.

Any desired drying system can be utilized. The present drying apparatus consists of a tower into which the concentrate fluid is sprayed. Air in the tower is heated. The concentrate fluid is sprayed in a pattern that causes the spray to swirl down the sides of the tower. As the spray travels down the sides of the tower, the water evaporates, producing powder particles including mineral elements. The powder falls downwardly to the bottom of the tower. Moist air travels upwardly through the center of the tower and is directed 23 to a bag house 22. The moist air enters elongate air-permeable hollow generally cylindrical bags in the bag house. The air travels outwardly through the walls of the bags and leaves behind powder particles on the inside surfaces of the bag. The bags are shaken each thirty seconds to cause the powder on the inner surfaces of the bag to fall downwardly for collection. Table I illustrates the mineral element concentration in the powder produced in dryer 15 when the liquid mineral element concentrate having the composition set forth in Table I was directed into dryer 15. The dry powder mineral element composition of Table I in aqueous solution has a pH of about 3.0.

In one spray system utilized in the dryer 15, the fluid concentrate is directed into dryer 15 under a pressure of about 2500 psi. The orifice size of the spray nozzles utilized is about 0.027 inch. The spray angle of the nozzle is 70 degrees and the average droplet size is about 75 microns.

The areas of application and product usage for the mineral element compositions of the invention include nutritional, personal care, and agricultural products. For example, in the area of nutritional products, the mineral element compositions resulting from the processes described herein can provide a broad spectrum mineral supplement to supplement minerals not derived from food consumption.

For example, the macro mineral elements found in the mineral element compositions of the invention are typically made up of all known macro mineral elements. These macro minerals are essential to bodily functions and are dependent on each other in the body and have been indicative for preventing disease. As a specific example, zinc acts as a cofactor to many enzymatic reactions such as DNA and RNA polymerase for the synthesis of proteins. Calcium is also a cofactor to the enzymes responsible for fat and protein metabolism. Calcium is believed to help prevent osteoporosis and colon cancer. Sodium and potassium are important for nerve transmission, muscle contraction, and balance of fluids in the body. Phosphorous is the second most abundant mineral in the body, after calcium, and plays many important roles in heart regularity, nerve impulses, and kidney function.

The trace or rare earth minerals also play an important role in body functions and have also been indicative of preventing disease. For example, copper helps make red blood cells, plays a role in bodily enzymes, and is important for the absorption of iron. Fluorine helps form bones and teeth, and helps make teeth decay-resistant. Iron deficiency is common throughout the world. Women are especially at risk, since they lose iron in menstrual blood. Deficiency can lead to anemia, with symptoms of fatigue, weakness and ill health. Iodine deficiency can result in goiter, the enlargement of the thyroid gland. Selenium is currently being investigated for its potential to prevent cancer.

In certain cases, supplementation of certain mineral elements can bring about improvements in disease states. For example, in the case of diabetes chromium, magnesium, and vanadium have been documented to improved diabetic disease state. Chromium is needed to make glucose tolerance factor, which helps insulin improve its action. Studies suggest that a deficiency in magnesium may worsen the blood sugar control in type 2 diabetes. Magnesium interrupts insulin secretion in the pancreas and increases insulin resistance in the body's tissues. Evidence suggests that a deficiency of Magnesium may contribute to certain diabetes complications. Vanadium has been clinically proven to normalize blood glucose levels in animals with type 1 and type 2 diabetes.

As people age, the ability to metabolize or absorb certain mineral elements decreases. People over age 65 have a greater risk of zinc deficiency due to a reduced ability to absorption, leading to other disease states. Zinc supplements may be required to avoid symptoms of deficiency, including anorexia, slow wound healing, impaired taste sensation or reduced immune function.

The use of a nutritional supplement in tablets, soft capsules, bars, processed foods or beverages which contains the small concentrations of the mineral element compositions described herein could be beneficial to health if used to supply sub-toxic dosages of certain mineral elements that can pose a toxic risk. An Acute Oral Toxicity animal study conducted at Northview Pacific Labs in Hercules, Calif. indicated that acute dosages of 1 gram of dry mineral element composition per kilogram of weight of an individual classified the Comprehensive Mineral Composition posed no toxicity risk to an individual. This qualifies the products produced by the processes of the invention as a unique composition that delivers a substantial natural balance of minerals through oral supplementation in a single or multiple dosages for human and veterinary product consumption.

The following examples are provided by way of explanation, and not limitation, of the invention.

EXAMPLE 1

Energy Powdered Nutritional Composition

| Component | % w/w |
| --- | --- |
| Cocoa | 26.00 |
| Vanillin | 1.00 |
| Sugar | 15.00 |
| Lecithin | 2.00 |
| Ground Oat | 12.00 |
| Soy Isolate | 40.00 |
| Dry (Powder) Mineral Element Composition Of Table I | 2.00 |
| Gum Arabic Spray Dry | 2.00 |

Procedure:
1. Dry-blend the ingredients above to prepare the nutritional formula composition.
2. In use of the composition, recommend 1 ounce of the composition per 8 ounces of cold milk.
3. Pack and preserve at 5-8° C. for use within 24 hours.

Mineral content of 1 Kilo of the Energy Powdered Nutritional Composition delivers no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 2

Nutritional Granola Bar

| Component | % w/w |
| --- | --- |
| Thick Rolled Oats | 34.00 |
| Sugar | 15.00 |
| Wheat Germ | 10.00 |
| Coconut | 10.00 |
| Honey | 10.00 |
| Silvered Almonds | 7.00 |
| Arabic FT Powder | 6.00 |
| Water | 7.00 |
| Dry Mineral Element Composition Of Table I | 1.00 |

Procedure:
1. Dry-blend all ingredients except water, honey and Arabic FT powder.
2. Mix the Arabic FT powder in water and honey.
3. Add the gum slurry to the dry blended ingredients and mold into desired shape.
4. Bake the mixture until oats are toasted to a light brown (about eight minutes at 300-320° F.)
5. Roll the baked bars and pack.

Mineral content of 1 Kilo of the Nutritional Granola Bar delivers no less than 1 ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 3

High Protein-Mineral Instant Drink Composition

| Component | % w/w |
| --- | --- |
| Cocoa | 13.00 |
| Vanillin | 0.50 |
| Non-Fat Dry Milk | 13.70 |
| Sugar | 50.00 |
| Lecithin | 1.00 |
| Soy Isolate | 20.00 |
| Dry Mineral Element Composition Of Table I | 1.00 |
| Gum Arabic Spray Dry | 0.80 |

Procedure:
1. Dry-blend the ingredients above;
2. 1 ounce per 8 ounces of cold milk using blend
3. Pack and preserve at 5-8° C. for use within 24 hours.

Mineral content of 1 Liter of High Protein-Mineral Instant Drink Composition delivers no less than ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 4

| Effervescent Tablet Mineral Composition | |
|---|---|
| Component | Weight |
| Tableting aids | 85.00 mg |
| Sodium Bicarbonate | 10.00 mg |
| Citric Acid | 4.00 mg |
| Dry Mineral Element Composition Of Table I | 1.00 mg |

Procedure:
Blend and Tablet Press.

Mineral content of 500 mg Effervescent Tablet Mineral Composition in 8 ounces of water delivers no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 5

| Vitamin E Soft Gelatin Capsule (400 IU Vit. E), Size 7.5 Oval | |
|---|---|
| | mg/capsule |
| Fill Material | |
| DL -Alpha Tocopheryl Aceate (1000 IU/g) | 400 mg |
| Soybean Oil | 45 mg |
| Beeswax | 10 mg |
| Hydrogenated Vegetable Oil | 40 mg |
| Dry Mineral Element Composition of Table I | 5 mg |
| Dry Gelatin Material | |
| Gelatin | 66 mg |
| Glycerin | 20 mg |
| Sorbitol | 20 mg |
| Water | 10 mg |

Procedure:
Compounding
1. Melt at 50-60° C. beeswax and the hydrogenated vegetable oil and soybean oil.
2. Mix and cool to 25-28° C., add Vitamin E and the Dry Mineral Element Composition.
3. Mix continuously before and during encapsulation.

Encapsulation
1. Fill using an encapsulating machine to form a number 7.5 oval capsule.
2. Dry to a moisture content of 8-10%.

Mineral content of one liter of Vitamin E Soft Gelatin Capsule Fill Material delivers no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 6

| Processed Food - Orange Juice | |
|---|---|
| Component | % w/w |
| Fresh Orange Juice | 98.80 |
| Potassium Sorbate | 0.15 |
| Vitamin E (Tocopherol) | 0.05 |
| Dry Mineral Element Composition Of Table I | 1.00 |

Procedure:
1. Using suitable press equipment, squeeze orange juice
2. Add and mix in Potassium Sorbate and Tocopherol
3. Add and mix Mineral Composition
4. Pack and chill at 5-8° C.

Mineral content of one liter of Processed Orange Juice delivers no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 7

Beverage Additive

Powdered Concentrate Mineral Pack

Package ¼ oz of the dry mineral element composition of Table I in foil pack.

Mixing the ¼ oz of dry mineral element composition in the foil pack into 12 ounces of any beverage including water delivers no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

In the area of topical application and delivery of minerals, there is growing evidence that transdermal delivery could be the best route to deliver therapeutic agents, particularly metal drugs. There is also great interest on skin for being the next frontier for better route of delivery of vitamins and minerals for improved systemic absorption and availability. For example, studies at the Graduate School of Science and Technology at Bond University in Australia demonstrated how the gastrointestinal tract presents a significant barrier to the efficient absorption of both orally administered and inject-able dietary essential trace minerals. Their studies indicate that presenting trace minerals which can penetrate the dermis permits their slow release from the skin with more efficient (relative to incipient toxicity) systemic delivery. Examples are given of dermal application of copper, zinc, titanium, platinum and gold complexes to treat chronic inflammatory disease. Some of these compounds are also anti-cancer agents. Other studies have demonstrated that skin penetration of minerals follow a pattern of organ distribution.

The inventors believe that the mineral element compositions described herein can be an ideal multi-mineral product for delivery through the skin qualifying as a unique composition that delivers a substantial natural balance of minerals to the surface of the skin or on stratum corneum for transdermal supplementation. A single or multiple dosage for human and veterinary product application onto the skin would contain small concentrations of the mineral element compositions described herein and could be beneficial to health if used in sub-toxic dosages.

An example of a transdermal product follows.

EXAMPLE 8

| Transdermal Mineral Gel Composition | |
|---|---|
| Ingredients | Weight % |
| Liquid mineral element composition of Table I | q.s. to 100% |
| Xanthan gum | 0.30 |
| Diethylene glycol monoethyl ether | 12.00 |
| Ethyl oleate | 2.00 |
| Alcohol SDA 40 | 7.00 |

Procedure:
1. Mix xantham gum in liquid mineral element composition using propeller mixer.
2. Add other ingredients one by one.

One Kilogram of Transdermal Mineral Gel Formula Composition will deliver onto the stratum corneum no less than 1 ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium, to be absorbed and bioavailable selectively by skin as it is delivered transdermally.

The resulting aqueous solutions from the mineral element composition are highly acidic. Preparation of acidic mineral element solutions can useful, particularly for the personal care industry.

An example of a low pH composition follows:

EXAMPLE 9

Water—100% as supplied through the process of reverse osmosis pH=5.7

EXAMPLE 10

Water: 95% by weight, as supplied through the process of reverse osmosis

Dry mineral element composition of Table I: 5% by weight

Mix water and mineral element composition together. The pH of the resulting aqueous solution is 3.0.

The mineral composition aqueous solution of Example 10 is substantially non-irritating to skin and eyes. Acidic solution will normally be irritating to open wounds. For example, aqueous solutions of glycolic acid with a pH=3.0 will sting or burn when applied or upon contact to freshly shaven skin. The pH=3.0 aqueous solution of Example #10 causes little or no sting or burning when applied to freshly shaven skin.

In the area of personal care products, minerals have been the subject of increased importance. Minerals play an important role in skin structure. As examples, zinc plays an important antioxidant role necessary for development of new cells and cell turnover or cellular proliferation. Silicon has been studied for its role in the formation of collagen, the skin underlying support. Copper is important in keratinization and in the production of enzymes. Selenium is important in maintaining skin elasticity. Minerals as used in baths, bath beads, mud treatments, masks, and facial mineral restoration products have been extensively used in the spa, salon, and retail cosmetic industry. "Dead Sea" minerals, colloidal minerals, and phyto-minerals have been used extensively for beautification and therapeutic purposes. The inventors believe that the mineral element composition described herein is novel for formulating products for cosmetic beautification using conventional procedures known to those who practice the art.

Examples of cosmetic beautification products follow.

EXAMPLE 11

| Mineral Mud Treatment Composition | |
|---|---|
| Ingredient | Weight % |
| Water: | q.s. to 100% |
| Xantham gum: | 0.50 |
| Kaolin: | 20.00 |
| Dry Mineral Element Composition: | 5.00 |

Procedure: Mix above components together to form facial mud composition. Apply mud composition to skin.

EXAMPLE 12

| Evian Facial Spray Composition | |
|---|---|
| Ingredient | Weight % |
| Evian Water: | 95 |
| Dry Mineral Element Composition Of Table I: | 5 |

Procedure: Admix water and mineral composition to form spray composition. Apply spray composition to face to wet skin.

EXAMPLE 13

| Soft Gel Gelatin Bath Beads Formula with inner fill material consisting of: | |
|---|---|
| Ingredient | Weight % |
| Mineral Oil | 40.00 |
| Petrolatum | 50.00 |
| Polyethylene Glycol 3350 | 9.00 |
| Dry Mineral Element Composition Of Table I | 1.00 |

Procedure:

Blend glycol, petrolatum, and mineral oil and add mineral element composition. Heat the composition to sixty-five degrees C. and mix. Cool to thirty-five degrees C. before encapsulation.

The compositions prepared in Examples 11 to 13 will deliver no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

Skin proliferation, the rate at which cell are born at the basal layer and subsequently shed from the body after reaching the upper layers of the stratum corneum, is an important and dynamic function for maintaining healthy skin. For example, psoriatic patients suffer from proliferation disorders as skin cells do not regenerate or desquamate normally. Because minerals such as zinc and copper play a role in skin proliferation, they have been extensively studied for topical application and have been shown to improve certain skin condition disorder. Skin proliferation disorders such as dandruff have also been studied with the use of minerals to bring about improvements.

Altering the rate of skin proliferation has been the mechanism by which many anti-aging skin care products are promoted. As skin ages the skin proliferation rate decreases, and stimulating cell renewal to a rate that is closer to younger skin has proven to improve the general appearance of skin. Ingredient such as retinoic acids, retinol and alpha hydroxy acids (AHA's) are widely promoted on a global scale for their ability to increase cell turnover and promote younger looking skin.

For these reasons AHA's are a commonly added to skin care products including moisturizers, cleanser, toners, and masks. AHA's are naturally derived from fruit and milk sugars and synthetically made as pharmaceutical and cosmetic acidulant ingredient. They are used in skin care as 'cosmeceutical' or functional cosmetic ingredients.

The most commonly used AHA's are glycolic acid and lactic acid. AHA's work mainly as an exfoliant of the skin. They cause the cells of the skin to become "unglued" allowing the dead skin cells at the surface of the skin to slough off, making room for re-growth of new skin. They also indirectly stimulate, through the process of irritation, the production of new cells. They have been reported to improve wrinkling, roughness, and pigmentation on skin after long term application and have been extensively studied.

AHA's as used in skin-care products work best at acidic pH's as it is the free acid and not the neutralized or salt counterparts that have been found effective on the skin as exfoliants. Typically, a pH of 3-5 is optimal when utilizing AHA's. As a result, two major side effects of AHA's are irritation and sun sensitivity. Symptoms of irritation include redness, burning, itching, pain, and possibly scarring. There are milder and other forms of exfoliants on the market today than AHA. Beta hydroxy acids such as salicylic acid have been reported to bring about skin cell turnover rate increases. Retinol (the alcohol form of retinoic acid) has also been extensively used.

It was unexpectedly found that the liquid mineral element composition and the dry powder mineral element composition produced in accordance with the invention, as well as solutions of the same, were able to cause skin to exfoliate. There appears to be no prior art suggesting any anticipatory use of minerals as skin exfoliants or to affect cell renewal.

Topical preparations that included the use of the mineral element compositions of the invention were observed to provide multiple skin benefits. Among the benefits observed was mild exfoliation. Exfoliation was subjectively measured by the ability of skin to be renewed after several days of use, with some mild peeling depending on subject. Skin was observed as less sallow and more translucent. Product containing 5% by weight of the dry powdered mineral element composition of Table I in aqueous solution was observed to provide the maximum exfoliation effect.

Typically, AHA products become irritating after several days of use as the skin becomes sensitized to low pH levels of these products. Comparatively, aqueous solutions including 5% by weight of the dry mineral element composition of Table I at a pH of 3 demonstrated the ability to exfoliate skin in a non-irritating manner.

It is therefore novel, at least for the mineral element compositions derived by the extraction process described herein, that the mineral element compositions can serve as a new class of cosmetic and dermatological ingredients of exfoliation with significantly less adverse effects such as burning and irritation.

The use of the comprehensive mineral composition in topical over the counter therapeutic products is believed to be beneficial to skin disorders ranging from severe dry skin to treatment of skin disorders. It is known that many macro and micro mineral elements play important roles in treating skin disorders. For example, copper is essential for production of tyrosinase, an enzyme which is required for the production of melanin for the activation of melanocytes which together with sunscreens protect the skin from UV by initiating tanning. As another example, selenium can help in the treatment and prevention of dandruff and deficiency in the mineral can lead to appearance of premature aging.

It is believed that the comprehensive mineral compositions described herein can be an ideal multi-mineral product for delivery on the skin qualifying as a unique composition that delivers a substantial natural balance of minerals in a single or multiple dosages for human and veterinary product consumption providing mild exfoliation effects:

Examples of additional skin care product compositions follow.

EXAMPLE 14

| Exfoliant Cleanser Composition | |
| --- | --- |
| Ingredient | Weight % |
| Liquid Mineral Element Composition Of Table I: | q.s. to 100% |
| TEA Cocoyl Glutamate | 7.00 |
| Glycerin | 5.00 |
| Decyl Glucoside | 5.00 |
| Dimethicone Copolyol Phosphate | 2.00 |
| Preservatives and Fragrance | 1.00 |

Procedure:

Blend each ingredient one at a time to produce final composition. Apply final composition to skin with or without water, gently rub composition into skin for at least 2 minutes, and rinse with water.

One liter of Exfoliant Cleanser Composition delivers onto the stratum corneum no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 15

| Suspended Minerals Exfoliant Scrub Composition | |
| --- | --- |
| Ingredients | Weight % |
| Phase A | |
| Water | q.s to 100% |
| Propylene Glycol | 5.00 |
| Phase B | |
| Hydrogenated Polyisobutene | 10.00 |
| Isopropyl Myristate | 5.00 |
| Mineral Oil | 3.00 |
| PEG 100 Stearate & Glyceryl Monostearate | 5.00 |
| Polysorbate 20 | 1.00 |
| Beeswax | 2.00 |
| Phase C | |
| Preservatives and Fragrance | 1.00 |
| Dry Mineral Element Composition of Table I | 20.00 |

Procedure:

1. Blend ingredients listed above under Phase A and heat to 75 C.
2. Blend ingredients listed above under Phase B and heat to 77 C.
3. Add Phase B to Phase A at 77 degrees C. and blend with propeller mixer to produce intermediate composition.
4. Cool intermediate composition to 40 C, and add ingredients listed above under Phase C to intermediate composition one ingredient at a time to produce final composition.
5. Cool final composition to 25 C. Apply final composition to skin with or without water, gently rub composition into skin for at least one minute, and rinse with water to exfoliate skin.

One liter of Suspended Minerals Exfoliant Scrub Composition delivers onto the stratum corneum no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 16

| Under Make-up Moisturizer Composition | |
|---|---|
| Ingredients | Weight % |
| Liquid Mineral Element Composition Of Table I | q.s to 100% |
| Glycerin | 5.00 |
| Xanthan Gum | 1.00 |
| Aloe Vera Gel | 1.00 |
| Hyaluronic Acid | 0.50 |
| Preservatives and Fragrance | 1.00 |

Procedure:

Blend ingredients together sequentially one at a time. Begin by blending glycerin with the liquid mineral element composition.

One Liter of Under Make-up Moisturizer Composition will deliver onto the stratum corneum no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 17

| Preservative-Free Cell Regenerative Gel Composition | |
|---|---|
| Ingredient | Weight % |
| Liquid Mineral Composition Of Table I | q.s. to 100% |
| Xanthan Gum | 1.0 |

Procedure:

Blend ingredients together at room temperature to form composition.

One Kilo of Cell Regenerative Gel Composition will deliver onto the stratum corneum no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 18

| Dandruff Shampoo Composition | |
|---|---|
| Ingredient | Weight % |
| Liquid Mineral Element Composition Of Table I | q.s. to 100% |
| Sodium Lauryl Sulphate | 20.00 |
| DEA Lauryl Sulphate | 2.00 |
| Cocamide DEA | 2.00 |
| Glycol Distearate | 1.00 |
| Preservatives and Fragrance | 1.00 |
| Zinc Pyrithione | 2.00 |

Procedure:

Blend ingredients together one at a time at 55 C. Begin by blending sodium lauryl sulphate with the liquid mineral composition. Use the final composition by wetting hair and apply a small amount in the same manner that conventional shampoos are applied. Then rinse with water. Before rinsing, allow the final composition to contact the scalp for at least one minute.

One Liter of Dandruff Shampoo Composition will deliver onto the stratum corneum no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 19

| Psoriatic Cream Composition | |
|---|---|
| Component | Weight % |
| Phase A | |
| Liquid Mineral Element Composition Of Table I | q.s. to 100% |
| Propylene Glycol | 2.0 |
| Hydroxyethyl cellulose | 1.0 |
| Phase B | |
| Isopropyl Palmitate | 5.0 |
| Petrolatum | 5.0 |
| Polowax | 4.0 |
| Phase C | |
| Coal Tar Solution | 10.00 |

Procedure:
1. Blend together the components listed above under Phase A and heat to 75 degrees C. to produce the Phase A composition.
2. Blend together the components listed above under Phase B and heat to 77 degrees C. to produce the Phase B composition.
3. Combine the Phase A and Phase B compositions and mix with a propeller mixer to produce an intermediate composition.
4. Cool the intermediate composition to 40 degrees C., and add to the intermediate composition one at a time the components listed above under Phase C to produce the final composition.
5. Cool the final composition from 40 degrees C. to 25 degrees C.

Apply the final composition to the dermis by gently rubbing small amounts into the dermis and allowing the final composition to remain on the dermis.

One Liter of Psoriatic Cream Composition will deliver onto the stratum corneum no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

Also unexpected in terms of skin care benefits was the ability of the liquid mineral element composition of Table I to minimize excess oil, minimize pore size, and balance skin tone both during application and over extended periods of time, this indicating that the mineral element composition was possibly affecting regulation of sebaceous glands.

EXAMPLE #20

| Antibacterial Exfoliant Toner Composition | |
|---|---|
| Ingredient | Weight Percent |
| Liquid Mineral Element Composition of Table I | q.s. to 100% |
| Hydroxyethyl cellulose | 1.00 |
| Ethyl Alcohol | 62.00 |

Procedure:
Blend ingredient together one at a time at room temperature to produce the exfoliant toner formula composition. Apply the resulting composition by gently rubbing a small amount into the dermis for about thirty seconds. Then rinse dermis to remove any remaining composition.

One liter of Antibacterial Exfoliant Toner Composition will deliver onto the stratum corneum no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

EXAMPLE 21

| Acne Liquid Composition | |
|---|---|
| Component | Weight % |
| Liquid Mineral Element Composition Of Table I | q.s. to 100% |
| Diethylene Glycol Monoethyl Ether | 10 |
| Salicylic Acid | 2 |

Procedure:
Blend ingredients together one at a time at room temperature. Begin by blending liquid mineral element composition with the ether. Apply the resulting composition by gently rubbing into the dermis for at least thirty seconds and then rinsing to remove excess composition.

One liter of Acne Liquid Composition will deliver onto the stratum corneum no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium, Zinc, Zirconium.

The process described herein for producing a comprehensive mineral composition has no waste products. The process does have residual wash water extract that s utilized on an organic farm to reconstitute minerals as part of a soil depletion restoration program. The agricultural applications and product by process for agricultural use claims should be covered.

The following example describes a tablet that can be produced for administration by placing the tablet under an individual's tongue and allowing the tablet to dissolve or by placing the tablet in the individual's mouth against the inner cheek and allowing the tablet to dissolve.

EXAMPLE 22

| Buccal or sublingual Mineral Tablet | |
|---|---|
| Ingredient | Weight in mg |
| Dry Mineral Element Composition Of Table I | 2.0 |
| Lactose | 86.0 |

-continued

| Buccal or sublingual Mineral Tablet | |
|---|---|
| Ingredient | Weight in mg |
| Sucrose | 87.0 |
| Acacia | 10.0 |
| Microcrystalline cellulose | 6.0 |
| Magnesium stearate | 1.0 |
| Purified water | q.s. |

Procedure
1. Pass the first four ingredients listed above through a 60 mesh screen and blend to produce a first intermediate composition.
2. Moisten the intermediate composition with sufficient water to produce a relatively stiff mass.
3. Pass the stiff mass through a number 8 screen to produce a second intermediate composition.
4. Dry the second intermediate composition at 40 degrees C.
5. Pass the dried second intermediate composition through a number 16 screen to produce a third intermediate composition.
6. Blend the third intermediate composition with the microcrystalline cellulose and the magnesium stearate to produce a fourth intermediate composition.
7. Use a heavy-duty tablet press to compress the fourth intermediate composition into tablets each weight 200 mg.

Administer each tablet by placing the tablet in an individual's mouth under the tongue or adjacent the inside of the cheek and by allowing the tablet to dissolve slowly.

EXAMPLE 23

| Mineral Enriched Shampoo | |
|---|---|
| Ingredient | Weight % |
| Water | q.s. to 100% |
| Liquid Mineral Element Composition Of Table I | 10.0 |
| TEA Lauryl Sulphate | 10.0 |
| Sodium Lauryl Sulphate | 25.0 |
| Cocomide DEA | 2.0 |
| Preservatives, colorants, fragrance | 2.0 |

Procedure:
Admix all ingredients and heat to sixty (60) degrees C. with moderate mixing for five minutes and cool to room temperature.

As would be appreciated by those of skill in the art, compositions can also be prepared that can be applied by placing the composition in an eye or in the nose of an individual or animal.

Having described my invention in such terms as to enable those skilled in the art to practice the invention, and having described the presently preferred embodiments thereof,

We claim:

1. A method for preparing an extracted mineral element composition consisting of:
one acid treatment step, a settling step, a separating step, and a concentrating step,
wherein the one acid treatment step consists of admixing a clay soil, a mixture of clay soils, or a mixture of clay soils and leonardite with water in an amount at least two times the weight of the soil and an acid to produce a water-acid-soil slurry, wherein the amount of acid is 0.25% to 7.5% of the weight of the water;
wherein the settling step consists of allowing solids from the water-acid-soil slurry to settle;
wherein the separating step consists of separating the liquid of the water-acid-soil slurry from the settled solids wherein the solids comprise substantially all of the silica and aluminum from the clay soil, mixture of clay soils, or a mixture of clay soils and leonardite, and
wherein the concentrating step consists of concentrating the separated liquid to form a liquid extracted mineral element composition comprising (i) calcium, chlorine, magnesium, manganese, phosphorous, potassium, silicon, and sodium, and (ii) a lower amount of silica and aluminum than the clay soil, a mixture of clay soils, or a mixture of clay soils and leonardite.

2. A method for preparing an extracted mineral element composition consisting of:
one acid treatment step, a settling step, a separating step, a concentrating step, and a drying step,
wherein the one acid treatment step consists of admixing a clay soil, a mixture of clay soils, or a mixture of clay soils and leonardite with water in an amount at least two times the weight of the soil and an acid to produce a water-acid-soil slurry, wherein the amount of acid is 0.25% to 7.5% of the weight of the water;
wherein the settling step consists of allowing solids from the water-acid-soil slurry to settle;
wherein the separating step consists of separating the liquid of the water-acid-soil slurry from the settled solids wherein the solids comprise substantially all of the silica and aluminum from the clay soil, mixture of clay soils, or a mixture of clay soils and leonardite,
wherein the concentrating step consists of concentrating the separated liquid to form a liquid extracted mineral element composition comprising (i) calcium, chlorine, magnesium, manganese, phosphorous, potassium, silicon, and sodium, and (ii) a lower amount of silica and aluminum than the clay soil, a mixture of clay soils, or a mixture of clay soils and leonardite, and
wherein the drying step consists of drying the concentrated liquid to form a dry extracted mineral element composition.

3. The method of claim 2, wherein drying comprises spray drying the liquid extracted mineral element composition.

4. The method of claim 1, wherein the pH of the extracted mineral element composition is less than 4.5.

5. The method of claim 1, wherein the water is purified by reverse osmosis.

6. The method of claim 1, wherein the acid is an edible acid.

7. The method of claim 6, wherein the edible acid is citric acid.

8. The method of claim 6, wherein the edible acid is phosphoric acid.

9. The method of claim 1, wherein the liquid is concentrated by reverse osmosis.

10. The extracted mineral element composition made by the method of claim 2.

11. A method for treating a clay soil, a mixture of clay soils, or a mixture of clay soils and leonardite, consisting of,
one acid treatment step, a settling step, a separating step, a concentrating step, and a drying step,
wherein the one acid treatment step consists of admixing a clay soil, a mixture of clay soils, or a mixture of clay soils and leonardite, with water in an amount at least two times the weight of the soil and an acid to produce a water-acid-soil slurry, wherein the amount of acid is 0.25% to 7.5% of the weight of the water;

wherein the settling step consists of allowing solids from the water-acid-soil slurry to settle;

wherein the separating step consists of separating the liquid of the water-acid-soil slurry from the settled solids wherein the solids comprise substantially all of the silica and aluminum from the clay soil, mixture of clay soils, or mixture of clay soils and leonardite;

wherein the concentrating step consists of concentrating the separated liquid to form a liquid extracted mineral element composition comprising a lower amount of silica and aluminum than the clay soil, a mixture of clay soils, or a mixture of clay soils and leonardite, and wherein the drying step consists of drying the concentrated liquid to form a dry extracted mineral element composition.

12. The method of claim 11, wherein drying comprises spray drying the liquid extracted mineral element composition.

13. The method of claim 11, wherein the pH of the extracted mineral element composition is less than 4.5.

14. The method of claim 11, wherein the acid is an edible acid.

15. The method of claim 14, wherein the edible acid is citric acid or phosphoric acid.

16. The method of claim 2, wherein the pH of the extracted mineral element composition is less than 4.5.

17. The method of claim 2, wherein the water is purified by reverse osmosis.

18. The method of claim 2, wherein the acid is an edible acid.

19. The method of claim 18, wherein the edible acid is citric acid.

20. The method of claim 18, wherein the edible acid is phosphoric acid.

21. The method of claim 2, wherein the liquid is concentrated by reverse osmosis.

* * * * *